(12) United States Patent
Barrows et al.

(10) Patent No.: US 11,191,462 B2
(45) Date of Patent: Dec. 7, 2021

(54) EYE-MOUNTABLE UNDERLID DEVICE FOR MEASURING AN ANALYTE

(71) Applicant: Verily Life Sciences LLC, Mountain View, CA (US)

(72) Inventors: Daniel Barrows, Sunnyvale, CA (US); Hojr Pisheh, Rohnert Park, CA (US); Jeffrey Linhardt, San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 335 days.

(21) Appl. No.: 15/870,588

(22) Filed: Jan. 12, 2018

(65) Prior Publication Data

US 2018/0199864 A1 Jul. 19, 2018

Related U.S. Application Data

(60) Provisional application No. 62/446,485, filed on Jan. 15, 2017, provisional application No. 62/446,481, filed on Jan. 15, 2017.

(51) Int. Cl.
*A61B 5/145* (2006.01)
*A61B 5/1477* (2006.01)
*A61B 5/00* (2006.01)

(52) U.S. Cl.
CPC ........ *A61B 5/1477* (2013.01); *A61B 5/14507* (2013.01); *A61B 5/6821* (2013.01);
(Continued)

(58) Field of Classification Search
CPC .................. A61B 5/14507; G02C 7/04–049
See application file for complete search history.

(56) References Cited

U.S. PATENT DOCUMENTS 4,614,413 A * 9/1986 Obssuth .................. G02C 7/04
351/159.02
4,850,689 A * 7/1989 Martin .................. G02C 7/048
351/159.74
(Continued)

FOREIGN PATENT DOCUMENTS

CA 2906871 A1 3/2016
CN 102727218 A 10/2012
WO WO 2016/052282 A1 4/2016

OTHER PUBLICATIONS

International Search Report issued in co-pending International Patent Application No. PCT/US2018/013521, ISA/RU, dated Apr. 12, 2018, 2 pages.
(Continued)

*Primary Examiner* — Meredith Weare
(74) *Attorney, Agent, or Firm* — McDonnell Boehnen Hulbert & Berghoff LLP

(57) ABSTRACT

An eye-mountable device includes layer(s) of polymer material defining a body. The body includes a first side and a second side extending from a first end to a second end. The first side opposes the second side and curves inwardly toward the second side. The second side curves outwardly away from the first side. The body includes an anterior surface and a posterior surface extending from the first side to the second side and from the first end to the second end. The anterior side opposes the posterior side. The posterior surface has a concave shape. The device includes a substrate in the body including a mounting platform disposed proximally to a middle of the second side. The device includes, on the mounting platform, electronics that interact with a biological environment and monitor health-related information. The body may have a thickness profile that prevents the device from undesired movement.

17 Claims, 7 Drawing Sheets

(52) U.S. Cl.
CPC .......... *A61B 5/002* (2013.01); *A61B 5/14532* (2013.01); *A61B 2560/0214* (2013.01)

(56) References Cited

U.S. PATENT DOCUMENTS

| | | | | |
|---|---|---|---|---|
| 5,606,378 | A * | 2/1997 | Van Meurs | G02C 7/043 351/159.02 |
| 2009/0203985 | A1* | 8/2009 | Ehrecke | A61B 3/16 600/398 |
| 2012/0140167 | A1* | 6/2012 | Blum | A61F 2/1624 351/159.34 |
| 2012/0245444 | A1 | 9/2012 | Otis et al. | |
| 2012/0289810 | A1* | 11/2012 | Ehrecke | A61B 3/16 600/398 |
| 2015/0085249 | A1 | 3/2015 | Abreu | |
| 2015/0173602 | A1* | 6/2015 | Barrows | A61B 3/101 600/345 |
| 2016/0003760 | A1* | 1/2016 | Etzkorn | G02C 11/10 205/122 |
| 2017/0216094 | A1* | 8/2017 | Reo | A61M 27/002 |

OTHER PUBLICATIONS

Written Opinion issued in co-pending International Patent Application No. PCT/US2018/013521, ISA/RU, dated Apr. 12, 2018, 4 pages.

* cited by examiner

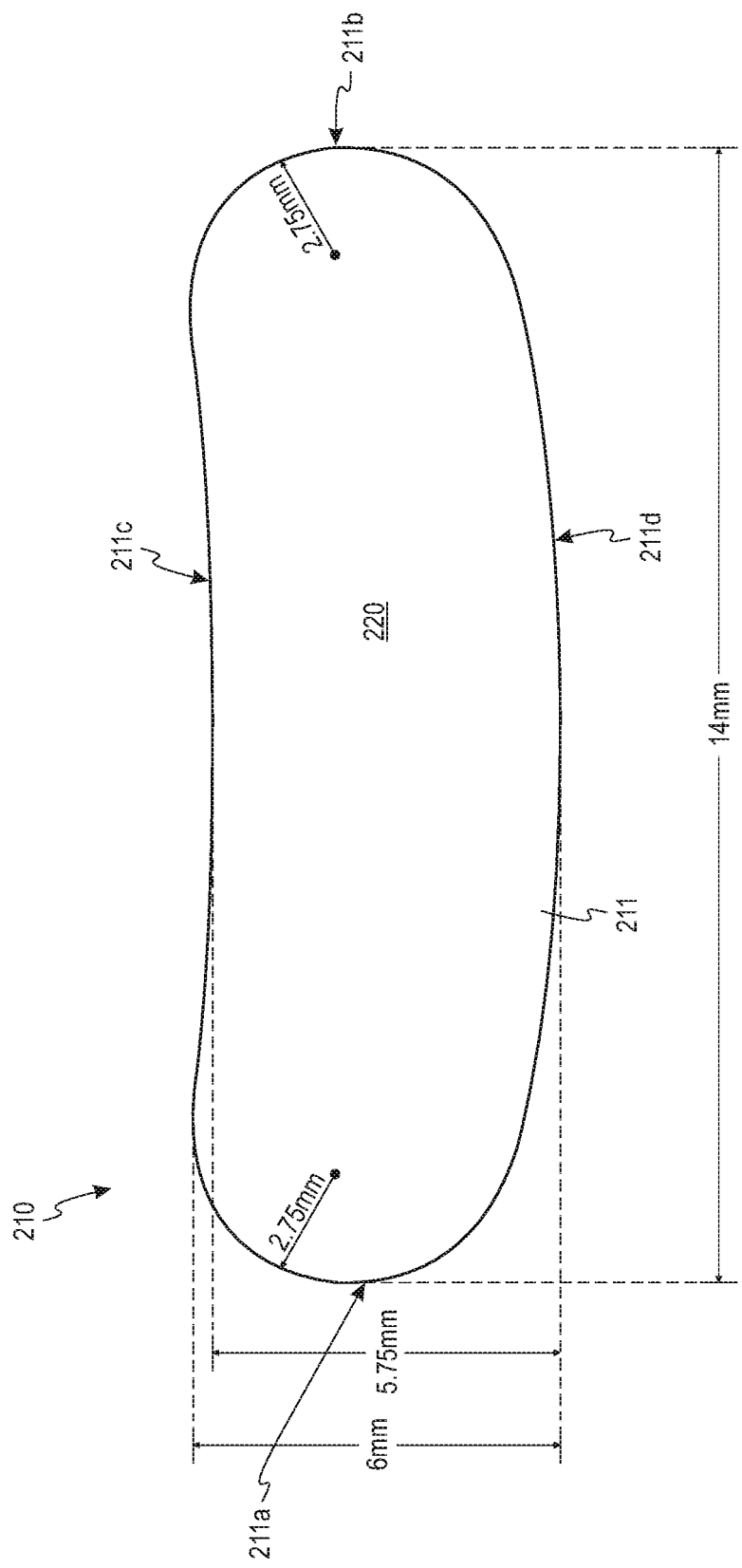

EYE-MOUNTABLE UNDERLID DEVICE FOR MEASURING AN ANALYTE

CROSS REFERENCE TO RELATED APPLICATIONS

The present application claims priority to U.S. Provisional Patent Application No. 62/446,481, filed on Jan. 15, 2017, and U.S. Provisional Patent Application No. 62/446,485, filed on Jan. 15, 2017, the contents of these application being hereby incorporated by reference in their entirety.

BACKGROUND

Unless otherwise indicated herein, the materials described in this section are not prior art to the claims in this application and are not admitted to be prior art by inclusion in this section.

A body-mountable device may monitor health-related information based on at least one analyte detected in a fluid of a user wearing the body-mountable device. For example, the body-mountable device may include an eye-mountable device in the form of a contact lens that includes a sensor to detect the at least one analyte (e.g., glucose) in a tear film of an eye.

SUMMARY

Disclosed herein are eye-mountable devices that can be positioned between an eyelid and a surface of an eye and, once positioned, monitor health-related information. Some embodiments are intended to be placed between a lower eyelid and the surface of the eye. Some embodiments are intended to be placed between an upper eyelid and the eye surface. Due to their positions under the lower and upper eyelids, respectively, these eye-mountable devices may be described as underlid devices. Advantageously, the underlid devices are deployed in positions that help minimize the effects of dehydration, mechanical agitation, light, and temperature.

According to an example embodiment, an eye-mountable device includes one or more layers of polymer material defining a body. The body includes a first side and a second side extending from a first end to a second end. The first side opposes the second side. The first side curves inwardly toward the second side. The second side curves outwardly away from the first side. The body includes an anterior surface and a posterior surface extending from the first side to the second side and from the first end to the second end. The anterior side opposes the posterior side. The posterior surface has a concave shape. The eye-mountable device includes a substrate in the body including a mounting platform disposed proximally to a middle of the second side. The eye-mountable device includes bio-interactive electronics mounted on the mounting platform. The bio-interactive electronics are operable to interact with a biological environment external to the body and to monitor health-related information.

According to another example embodiment, a method for deploying an eye-mountable device includes orienting a body of an eye-mountable device relative to an eye of a user. Orienting the body includes positioning a first end of the body closer to a nose of the user; positioning a second end of the body closer to a temple of the user; facing a posterior surface of the body toward the eye of the user; and facing an anterior surface of the body away from the eye of the user. The method includes positioning the oriented body between an eyelid of the user and the eye of the user. The posterior surface of the body is positioned against the eye and the anterior surface is positioned against the eyelid. The method includes operating bio-interactive electronics disposed in the body to interact with an environment external to the body and monitor health-related information. The body includes a first side and a second side extending from the first end to the second end. The first side opposes the second side. The first side curves inwardly toward the second side. The second side curves outwardly away from the first side. The eye-mountable device includes a substrate in the body. The substrate includes a mounting platform disposed proximally to a middle of the second side. The bio-interactive electronics are mounted on the mounting platform. The bio-interactive electronics are operable to interact with a biological environment external to the body and to monitor health-related information.

Additionally, underlid devices may have a thickness profile where the thicker region(s) of the thickness profile enhance on-eye stability and prevent the underlid devices from undesired movement to other parts of the eye.

According to an example embodiment, an eye-mountable device includes one or more layers of polymer material defining a body. The body includes a first side and a second side extending from a first end to a second end. The first side opposes the second side. The first side curves inwardly toward the second side. The second side curves outwardly away from the first side. The body includes an anterior surface and a posterior surface extending from the first side to the second side and from the first end to the second end. The anterior side opposes the posterior side. The posterior surface has a concave shape. The body includes a thickness profile defined by thicknesses from the anterior surface to the posterior surface. The thickness profile includes a first thickness region having a first thickness range and a second thickness region having a second thickness range. The first thickness region extends along the first side. The second thickness region extends proximately along the second side and is disposed between the second side and the first thickness region. The second thickness range has at least one thickness that is greater than the first thickness range. The eye-mountable device also includes bio-interactive electronics disposed in the body. The bio-interactive electronics are operable to interact with a biological environment external to the body and to monitor health-related information.

According to another example embodiment, a method for deploying an eye-mountable device includes orienting a body of an eye-mountable device relative to an eye of a user. Orienting the body includes positioning a first end of the body closer to a nose of the user; positioning a second end of the body closer to a temple of the user; facing a posterior surface of the body toward the eye of the user; and facing an anterior surface of the body away from the eye of the user. The method also includes positioning the oriented body between an eyelid of the user and the eye of the user. The posterior surface of the body is positioned against the eye and the anterior surface is positioned against the eyelid. The method also includes operating bio-interactive electronics disposed in the body to interact with an environment external to the body and monitor health-related information. The body includes a first side and a second side extending from the first end to the second end, the first side opposing the second side. The first side curves inwardly toward the second side. The second side curves outwardly away from the first side. The body includes a thickness profile defined by thicknesses between the anterior surface and the posterior surface. The thickness profile includes a first thickness region having a first thickness range and a second thickness region having a second thickness range. The first thickness region extends along the first side. The second thickness region extends proximately along the second side and is disposed between the second side and the first thickness region. The second thickness range for the second thickness region has at least one second thickness that is greater than the first thickness range for the first thickness region. The second thickness region stabilizes the position of the body between the eyelid and the eye.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 3A illustrates an anterior view of an example configuration for an underlid device that is intended to be placed between a lower eyelid and an eye surface, according to aspects of the present disclosure.

DETAILED DESCRIPTION

Figure 1:
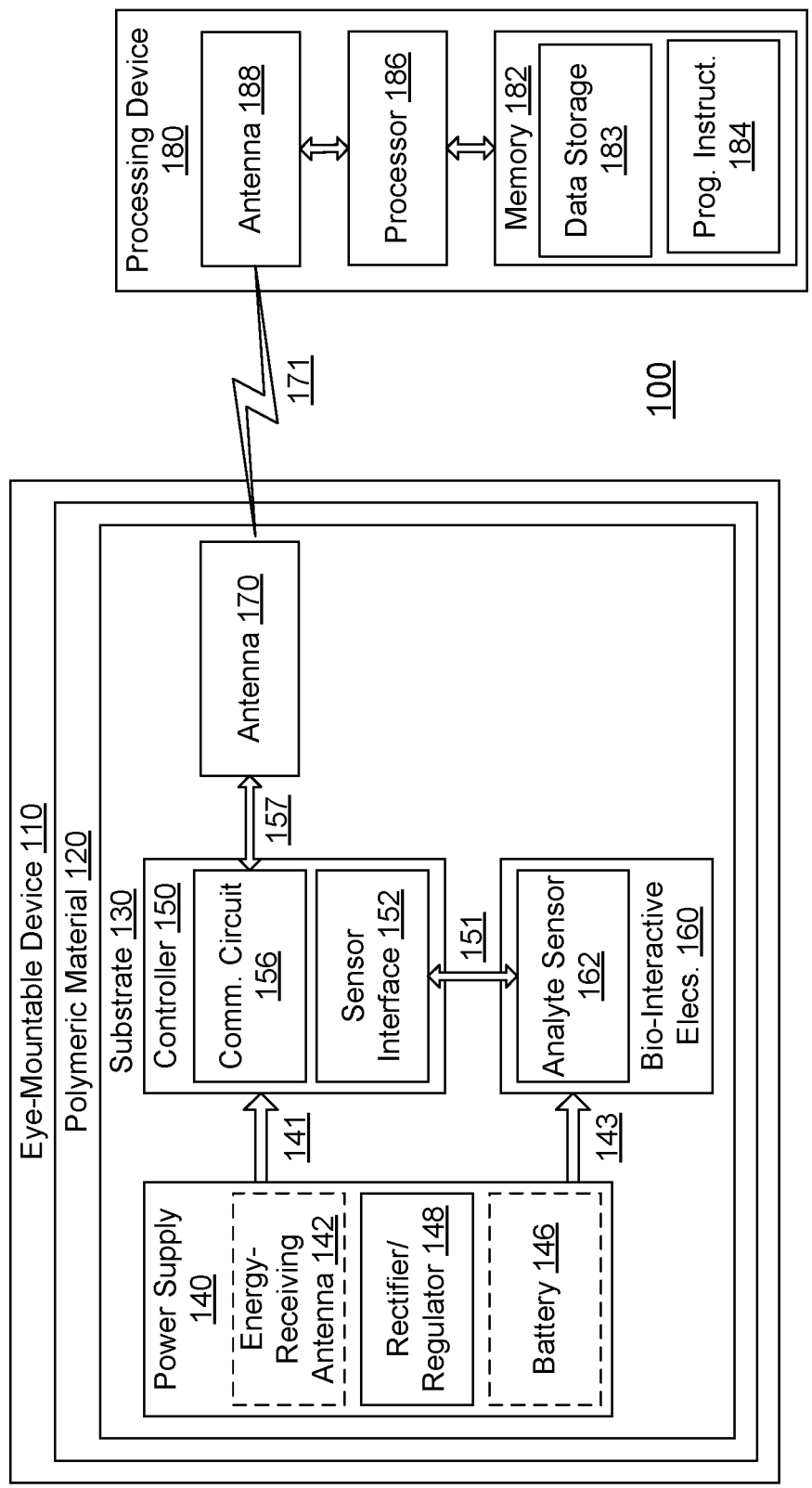
FIG. 1 illustrates a block diagram of an example system that includes an eye-mountable device in wireless communication with an external processing device, according to aspects of the present disclosure.

The following detailed description describes various features and functions of the disclosed systems and methods with reference to the accompanying figures. In the figures, similar symbols typically identify similar components, unless context dictates otherwise. The illustrative system and method embodiments described herein are not meant to be limiting. It will be readily understood that certain aspects of the disclosed systems and methods can be arranged and combined in a wide variety of different configurations, all of which are contemplated herein.

I. Introduction

According to aspects of the present disclosure, an eye-mountable device can be mounted on an eye of a user and can interact with a biological environment to monitor health-related information for the user. An example eye-mountable device includes a power supply, a controller, bio-interactive electronics, and a communication antenna. The eye-mountable device employs the bio-interactive electronics to monitor health-related information. The eye-mountable device employs the communication antenna to communicate information to/from the eye-mountable device. For instance, the communication antenna may be employed to communicate the health-related information to a external processing device via wireless signals for further processing, presentation, and/or other task(s). The controller controls the operation of the bio-interactive electronics and the communication antenna. The power supply supplies operating voltages to the controller and the bio-interactive electronics.

To monitor the health-related information, the bio-interactive electronics may include an analyte sensor that measures the concentration of an analyte in a tear film on the surface of the eye. The analyte sensor is preferably deployed in an environment that minimizes the effects of dehydration, mechanical agitation, light, and temperature. Such effects may reduce the accuracy of the sensor readings by the analyte sensor or otherwise result in poor operation by the eye-mountable device. Dehydration can affect the sampling by the analyte sensor and generate greater noise in the signals from the analyte sensor. Mechanical agitation can also generate additional signal noise and/or negatively affect sensitive electrochemical reactions for the analyte sensor. Meanwhile, light may affect sensitive electronics, and variations in temperature may affect the rate of electrochemical reactions in the analyte sensor and may result in an inaccurate calibration of the analyte sensor.

The effects of dehydration, mechanical agitation, light, and temperature may depend on the position of the eye-mountable device during operation. Some embodiments of the eye-mountable device are intended to be placed between a lower eyelid and the surface of the eye. Other embodiments of the eye-mountable device are intended to be placed between an upper eyelid and the eye surface. Due to their positions under the lower and upper eyelids, respectively, these embodiments may be described as underlid devices.

Such underlid devices are shaped in such a way as to be positioned stably under the lower eyelid or upper eyelid. Advantageously, the positions of the underlid devices allow their analyte sensors to be submerged, or otherwise maintain sufficient contact with, a tear film on the eye surface to keep their analyte sensors sufficiently hydrated. Additionally, due to their fit under the eyelids, the underlid devices can resist movement and may experience less mechanical agitation, e.g., due to blinking. The eyelids block the underlid devices from exposure to light. Furthermore, the regions between the eyelids and the eye surface provide more stable temperatures.

The underlid devices can also be positioned below or above the cornea to limit obstruction of the user's sightline. Moreover, the underlid devices when worn may be hidden under the lower eyelid or the upper eyelid and can thus be used more discretely by the user.

According to aspects of the present disclosure, underlid devices may have a thickness profile where the thicker region(s) of the thickness profile enhance on-eye stability and prevent the underlid devices from undesired movement to other parts of the eye.

II. Example System with Eye-Mountable Device

FIG. 1 illustrates a block diagram of an example system 100 with an eye-mountable device 110 in wireless communication with an external processing device 180. The eye-mountable device 110 can be mounted on an eye of a user and can interact with a biological environment to monitor health-related information for the user. The eye-mountable device 110 can also communicate the health-related information to the external processing device 180 for further processing or other task(s).

The outer surfaces of the eye-mountable device 110 may be formed from a polymeric material 120 that allows the eye-mountable device 110 to be mounted over a surface of the eye. In some embodiments, the polymeric material 120 may include one or more polymer layers that define aspects of the body of the eye-mountable device 110. The polymeric material 120 may define a concave posterior surface that can adhere to the eye surface by capillary forces produced by a tear film coating the eye surface. Additionally or alternatively, the eye-mountable device 110 can adhere to the eye surface by a vacuum force between the posterior surface and the eye surface resulting from the concave curvature.

As used throughout this disclosure, the posterior side of the eye-mountable device 110 refers to an inward-facing side of the eye-mountable device 110. Meanwhile, an anterior side of the eye-mountable device 110 refers to an outward-facing side of the eye-mountable device 110. As such, when the eye-mountable device 110 is mounted on an eye of the user, the posterior side corresponds to the side of the eye-mountable device 110 that contacts the eye of the user, and the anterior side corresponds to the side of the eye-mountable device 110 that faces away from the eye and does not contact the eye of the user.

The polymeric material 120 may include one or more biocompatible materials, such as those employed for use in contact lenses or other ophthalmic applications involving direct contact with the eye surface. For instance, the polymeric material 120 may include transparent silicone. The polymeric material 120 may be formed wholly or partially from such biocompatible materials. The polymeric material 120 may include an outer coating with such biocompatible materials. The polymeric material 120 may include materials that can maintain moisture at the eye surface, such as hydrogels and the like. In some instances, the polymeric material 120 can be a deformable ("non-rigid") material to enhance wearer comfort.

A substrate 130 is embedded or otherwise disposed in the polymeric material 120 and includes one or more surfaces for mounting a power supply 140, a controller 150, bio-interactive electronics 160, and a communication antenna 170. The eye-mountable device 110 employs the bio-interactive electronics 160 to interact with the eye's biological environment and to monitor health-related information. The eye-mountable device 110 employs the communication antenna 170 to communicate information to/from the eye-mountable device 110. For instance, the communication antenna 170 may be employed to communicate the health-related information to the external processing device 180 via wireless signals 171 for further processing, presentation, and/or other task(s). The controller 150 controls the operation of the bio-interactive electronics 160 and the communication antenna 170. The power supply 140 supplies operating voltages to the controller 150 and the bio-interactive electronics 160.

The substrate 130 may be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. For instance, the controller 150 is connected to the bio-interactive electronics 160 via interconnects 151 and to the communication antenna 170 via interconnects 157. The interconnects 151, 157 may formed by depositing suitable patterns of conductive materials on the substrate 130. Additionally, the communication antenna 170 may be formed by depositing a pattern of gold or another conductive material on the substrate 130. A combination of resists, masks, and deposition techniques may be employed to pattern materials on the substrate 130.

The substrate 130 may be formed from a relatively rigid polymeric material, such as polyethylene terephthalate (PET), parylene, or other material sufficient to structurally support the circuitry and/or electronics within the polymeric material 120. The eye-mountable device 110 may alternatively be arranged with a group of unconnected substrates rather than a single substrate. For instance, the controller 150 and the bio-interactive electronics 160 may be mounted to one substrate, while the communication antenna 170 may be mounted to another substrate and the two substrates can be electrically connected via the interconnects 157.

The power supply 140 may also be electrically coupled to the controller 150 and the bio-interactive electronics 160 via interconnects. The power supply 140 may include an energy-receiving antenna 142 that captures energy, via radio frequency radiation, provided by a wireless power source. In particular, the external processing device 180 may act as the wireless power source, however, the energy-receiving antenna 142 may additionally or alternatively capture energy from other wireless power sources.

In some embodiments, the communication antenna 170 may be a dual-purpose antenna. In addition to communicating information between the eye-mountable device 110 and the external processing device 180, the communication antenna 170 also functions as the energy-receiving antenna 142 to captures energy the external processing device 180 via the wireless signals 171. For instance, a loop antenna can both capture radiation for power transmission and communicate information via backscatter radiation.

The power supply 140 may also include a rectifier/regulator 148 to condition the captured energy to a stable DC supply voltage 141 that can be supplied to the controller 150 and the bio-interactive electronics 160. After the energy-receiving antenna 142 receives the radiation, varying electrical signals on the leads of the energy-receiving antenna 142 are output to the rectifier/regulator 148. The rectifier/regulator 148 rectifies the varying electrical signals to a DC voltage and regulates the rectified DC voltage to a level suitable for operating the controller 150 and the bio-interactive electronics 160. The rectifier/regulator 148 may include one or more energy storage devices (e.g., capacitors, inductors, etc.) arranged to mitigate high frequency variations in the energy-receiving antenna 142. For instance, an energy storage device may be connected to the output of the rectifier/regulator 148 to function as a low-pass filter. Accordingly, power from the energy-receiving antenna 142 is delivered, via the rectifier/regulator 148, to the controller 150 and the bio-interactive electronics 160.

Additionally or alternatively, the power supply 140 may provide the DC supply voltage 141 from a battery 146. In some embodiments, the battery 146 may be a single-use battery. In other embodiments, the battery 146 may be a rechargeable battery. As such, the energy-receiving antenna 142 may be employed to capture energy from a wireless power source to recharge the rechargeable battery 146. Additionally, the rectifier/regulator 148 may receive the output from the energy-receiving antenna 142 and generate a recharging voltage 143 for the rechargeable battery. Accordingly, power from the energy-receiving antenna 142 can be delivered indirectly to the controller 150 and the bio-interactive electronics 160 by initially storing the power in the rechargeable battery. The controller 150 can remain active as long as it receives the DC supply voltage 141.

The controller 150 may include logic circuitry that causes the bio-interactive electronics 160 to interact with the biological environment of the eye-mountable device 110. In particular, the bio-interactive electronics 160 may include an analyte sensor 162 that detects an analyte in the biological environment, where a concentration of the analyte indicates health-related information for the user. The controller 150 may include a sensor interface module 152 that operates the analyte sensor 162.

Accordingly, the example system 100 may be operated to monitor the analyte concentration in a tear film on the surface of the eye where the eye-mountable device 110 is mounted. The tear film is an aqueous layer secreted from the lacrimal gland to coat the eye. The tear film is in contact with the blood supply through capillaries in the structure of the eye and includes many biomarkers found in blood that can be analyzed to characterize a person's health. For instance, the tear film includes glucose, calcium, sodium, cholesterol, potassium, among other biomarkers. The concentrations of a biomarker in the tear film may be systematically different than the corresponding concentration of the same biomarker in the blood, but a relationship between the two concentration levels can be established to map tear film biomarker concentration levels to blood concentration levels. In particular, the tear film concentration of glucose can be established (e.g., empirically determined) to be approximately one tenth the corresponding blood glucose concentration. Thus, measuring tear film analyte concentration levels provides a non-invasive technique for monitoring biomarker levels in comparison to blood sampling techniques that require invasively drawing a volume of blood to be analyzed outside a person's body. The example system 100 can be operated to enable real time monitoring of analyte concentrations.

In some embodiments, the analyte sensor 162 may be an amperometric electrochemical sensor that includes a working electrode and a reference electrode. Application of an appropriate voltage between the working and reference electrodes causes an analyte in the biological environment to undergo electrochemical reactions (e.g., reduction and/or oxidation reactions) at the working electrode and to generate an amperometric current. The amperometric current may depend on the concentration of the analyte in the biological environment, and thus the amount of amperometric current can provide an indication of analyte concentration. In some embodiments, the sensor interface module 152 may be a potentiostat configured to apply a voltage difference between the working and reference electrodes while measuring a current through the working electrode.

In some cases, a reagent may be employed to sensitize the electrochemical sensor to desired analytes. For instance, a layer of glucose oxidase ("GOX") can be applied at or around the working electrode to catalyze glucose into hydrogen peroxide ($H_2O_2$). The hydrogen peroxide can then be oxidized at the working electrode, thereby releasing electrons to the working electrode and generating a current.

$$glucose + O_2 \xrightarrow{GOX} H_2O_2 + gluconolactone$$

$$H_2O_2 \rightarrow 2H^+ + O_2 + 2e^-$$

The current generated by either reduction or oxidation reactions may be approximately proportionate to the reaction rate. Further, the reaction rate may be dependent on the rate of analyte molecules reaching the electrochemical sensor electrodes to fuel the reduction or oxidation reactions, either directly or catalytically through the reagent. In a steady state, where analyte molecules diffuse to the electrochemical sensor electrodes from a sampled region at approximately the same rate at which additional analyte molecules diffuse to the sampled region from surrounding regions, the reaction rate is approximately proportional to the concentration of the analyte molecules. The current thus provides an indication of the analyte concentration.

To measure an analyte concentration with the example system 100, the eye-mountable device 180 is mounted on the surface of the eye. The power supply 140 delivers power to the controller 150 as described above and activates the electronic components of the eye-mountable device 110. Upon receiving the power, the controller 150 can operate the analyte sensor 162 to measure an analyte concentration level. For instance, the sensor interface module 152 can apply a voltage between a working electrode and a reference electrode in the analyte sensor 162 sufficient to cause the analyte to undergo an electrochemical reaction at the working electrode. The current through the working electrode can be measured to provide the sensor output indicative of the analyte concentration.

In some embodiments, power can be non-continuously ("intermittently") supplied to the controller 150 and bio-interactive electronics 160. For instance, the external processing device 180 may be operated at specified times to transmit radio frequency radiation to the energy-receiving antenna 142 and activate the eye-mountable device 110 long enough to carry out an analyte concentration measurement and communicate the sensor readings. In particular, the radio frequency radiation can provide sufficient power to charge two electrodes to a potential sufficient to induce electrochemical reactions, measure the resulting amperometric current, and modulate the antenna in a manner indicative of the measured current. In such an example, the radio frequency radiation can also be considered an interrogation signal from the external processing device 180 to the eye-mountable device 110 to request measurement(s). By periodically interrogating the eye-mountable device 110, i.e., supplying the radio frequency radiation to temporarily activate the eye-mountable device 110, and storing the sensor readings (e.g., via the data storage 183), the external processing device 180 can collect a set of analyte concentration measurements over time without continuously powering the eye-mountable device 110.

As described above, in some embodiments, the battery 146 may be employed to provide power to the controller 150. In some embodiments, the battery 146 may reduce or eliminate the need for radio frequency radiation from the external processing device 180 to activate the eye-mountable device 110. As such, the battery 146 allows the eye-mountable device 110 to be operated autonomously. The battery 146 may bias the analyte sensor 162, via a potentiostat, so that electrodes in the analyte sensor 162 are at appropriate potentials for analyte measurement. Additionally, the battery 146 may power the controller 150 to store sensor readings from the analyte sensor 162 for subsequent communication to the external processing device 180.

As described above, the controller 150 can communicate with the external processing device 180 via the communication antenna 170. The controller 150 may include a communication circuit 156 for sending and/or receiving information via the communication antenna 170. The communication circuit 156 may include one or more oscillators, mixers, frequency injectors, etc. to modulate and/or demodulate information on a carrier frequency to be transmitted and/or received by the communication antenna 170.

Accordingly, the controller 150 may communicate sensor readings from the analyte sensor 162 by modulating an impedance of the communication antenna 170 in a manner that is perceivable by the external processing device 180. In particular, the communication circuit 156 may cause variations in the amplitude, phase, and/or frequency of backscatter radiation from the communication antenna 170, and such variations can be detected by the external processing device 180.

Correspondingly, the external processing device 180 may include an antenna 188 to send/receive wireless signals 171 to/from the eye-mountable device 110. The wireless signals 171 may include radio frequency radiation to power the eye-mountable device 110 as well as signals for communicating information, e.g., the sensor readings, between the eye-mountable device 110 and the external processing device 180. In some cases, the external processing device 180 may be positioned in sufficient proximity to the eye-mountable device 110 to allow this wireless communication.

The external processing device 180 may also include a computing system with a processor 186 in communication with a memory 182. The memory 182 may be a non-transitory computer-readable medium that can include, without limitation, magnetic disks, optical disks, organic memory, and/or any other volatile (e.g., RAM) or non-volatile (e.g., ROM) storage system readable by the processor 186. The memory 182 may include a data storage 183 to store indications of data structures, such as sensor readings (e.g., from the analyte sensor 162), program settings (e.g., to adjust behavior of the eye-mountable device 110 and/or external processing device 180), etc.

The external processing device 180 may also include one or more hardware components for operating the antenna 188 to send and receive the wireless signals 171. For example, oscillators, frequency injectors, encoders, decoders, amplifiers, filters, etc. can drive the antenna 188 according to instructions from the processor 186.

The memory 182 may also include program instructions 184 for execution by the processor 186 to cause the external processing device 180 to perform processes specified by the program instructions 184. For example, the program instructions 184 can cause the external processing device 180 to display or otherwise present, via a user interface, information communicated from the eye-mountable device 110 (e.g., sensor readings from the analyte sensor 162).

In some embodiments, the external processing device 180 may be implemented as a smart phone, smart device, digital assistant, or other portable computing device with wireless connectivity sufficient to provide the wireless communication via the signals 171. In alternative embodiments, the external processing device 180 may be implemented as an antenna module that can be plugged into a portable computing device, for instance, where the communication link 171 operates at carrier frequencies not commonly employed in portable computing devices. In further embodiments, the external processing device 180 may be implemented as a special-purpose device that allows the wireless communication link 171 to operate with a low power budget. For instance, the external processing device 180 may be integrated in eyeglasses, integrated in a piece of jewelry such as a necklace, earing, etc., or integrated in an article of clothing worn near the head, such as a hat, headband, etc.

It is noted that aspects of FIG. 1 are described in connection with functional modules for convenience in description. However, embodiments of the eye-mountable device 110 can be arranged with one or more of the functional modules ("sub-systems") implemented in a single chip, integrated circuit, and/or physical feature. For example, while the rectifier/regulator 148 is illustrated in the power supply block 140, the rectifier/regulator 148 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided on a chip by rectifier and/or regulator components of the same chip. That is, the functional blocks in FIG. 1 shown as the power supply block 140 and controller block 150 need not be implemented as separated modules. Moreover, one or more of the functional modules described in FIG. 1 can be implemented by separately packaged chips electrically connected to one another.

III. Example Implementation of Eye-Mountable Device as an Underlid Device

As described above, the eye-mountable device 110 employs the analyte sensor 162 that performs analyte concentration measurements to monitor health-related information. The analyte sensor 162 is preferably deployed in an environment that minimizes the effects of dehydration, mechanical agitation, light, and temperature. Such effects may reduce the accuracy of the sensor readings by the analyte sensor 162 or otherwise result in poor operation by the eye-mountable device 110. Dehydration can affect the sampling by the analyte sensor 162 and generate greater noise in the signals from the analyte sensor 162. Mechanical agitation can also generate additional signal noise and/or negatively affect sensitive electrochemical reactions for the analyte sensor 162. Meanwhile, light may affect sensitive electronics, and variations in temperature may affect the rate of electrochemical reactions in the analyte sensor 162 and may result in an inaccurate calibration of the analyte sensor 162.

Figure 2A:
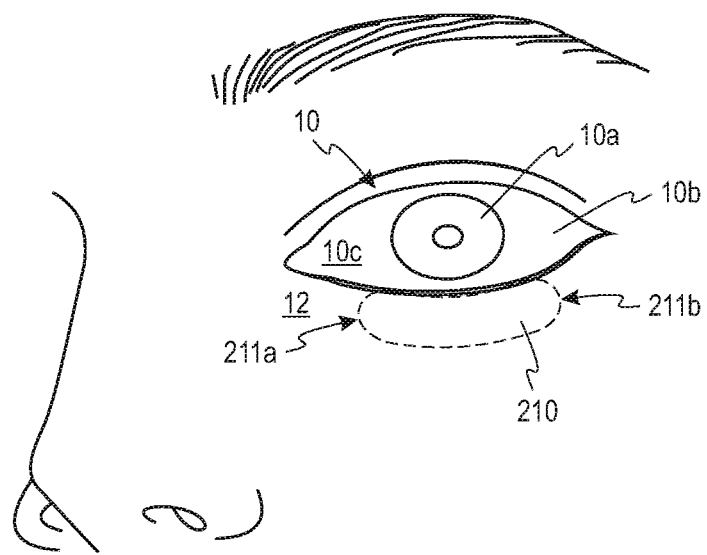
FIG. 2A illustrates an example implementation of an eye-mountable device as an underlid device that is positioned between a lower eyelid and an eye surface, according to aspects of the present disclosure.
Figure 2B:
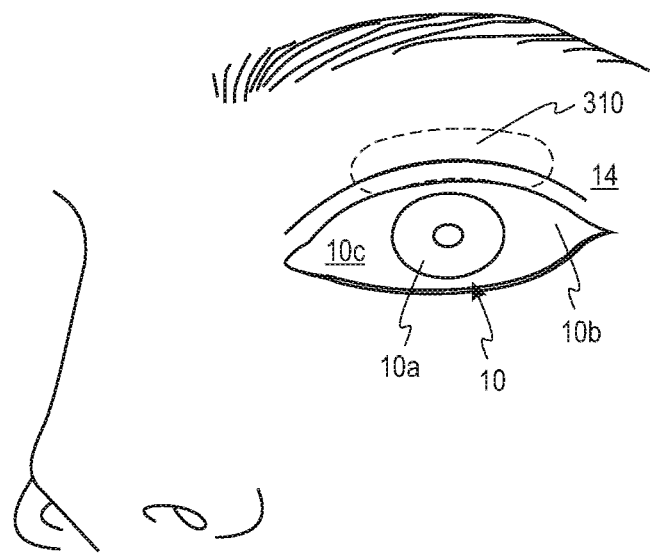
FIG. 2B illustrates another example implementation of an eye-mountable device as an underlid device that is positioned between an upper eyelid and an eye surface, according to aspects of the present disclosure.

The effects of dehydration, mechanical agitation, light, and temperature may depend on the position of the eye-mountable device 110 during operation. FIGS. 2A-B illustrate example implementations for the eye-mountable device 110, where these effects are minimized. In FIG. 2A, an embodiment 210 of the eye-mountable device 110 is positioned between a lower eyelid 12 and a surface 10c of an eye 10. In FIG. 2B, an embodiment 310 of the eye-mountable device 110 is positioned between an upper eyelid 14 and the eye surface 10c. Due to their positions under the lower and upper eyelids, respectively, the embodiments 210, 310 are described herein as underlid devices.

The underlid devices 210, 310 are shaped so as to be positioned stably under the lower eyelid 12 and upper eyelid 14, respectively. Advantageously, the positions of the underlid devices 210, 310 allow their analyte sensors to be submerged, or otherwise maintain sufficient contact with, a tear film on the eye surface 10c to keep their analyte sensors sufficiently hydrated. Additionally, due to their fit under the eyelids 12, 14, the underlid devices 210, 310 can resist movement and may experience less mechanical agitation, e.g., due to blinking. The lower eyelid 12 or the upper eyelid 14 block the underlid devices, 210, 310 from exposure to light. Furthermore, the regions between the eyelids 12, 14 and the eye surface 10c provide more stable temperatures.

In contrast, eye-mountable devices that have form factors similar to conventional contact lenses, i.e., positioned over the cornea of the eye, have disadvantages. Because they are not covered by the lower eyelid 12 or the upper eyelid 14, such devices are exposed to air, light, and external conditions. In particular, too much exposure to air may cause the analyte sensor to experience dehydration. Further, the analyte sensor may not remain in sufficient contact with the tear film to prevent dehydration. Such devices may also be more susceptible to mechanical agitation due to blinking and may experience greater temperature fluctuation due to greater exposure to air and external conditions.

Advantageously, the underlid devices 210, 310 are also positioned below or above the cornea 10a to limit obstruction of the user's sightline. Moreover, the underlid devices 210, 310 when worn may be hidden under the lower eyelid 12 or the upper eyelid 14 and can thus be used more discretely by the user.

FIG. 3A illustrates an anterior view of the underlid device 210. The underlid device 210 includes a body 211 that is defined by a polymeric material 220, which corresponds to the polymeric material 120 described above. The body 211 extends from a nasal end 211a to a temporal end 211b. When the underlid device 210 is deployed between the lower eyelid 12 and the eye surface 10c, the underlid device 210 is oriented as shown in FIG. 2A so that the nasal end 211a is positioned closer to the nose of the user and the temporal end 211b is positioned closer to the temple of the user. In some embodiments, for instance, the distance between the nasal end 211c and the temporal end 211d may be approximately 14 mm. Although the underlid device 210 appears to be symmetric about one axis in FIG. 3A, embodiments are not necessarily symmetric.

At the nasal end 211a, the body 211 curves outwardly (away from the temporal end 211b). Similarly, at the temporal end 211b, the body 211 curves outwardly (away from the nasal end 211a). The radius/radii of curvature at the temporal end 211b may be similar to the radius/radii of curvature at the nasal end 211a. In some embodiments, for instance, the radius of curvature at the nasal end 211a and the temporal end 211b may be approximately 2.75 mm.

The body 211 also includes an upper side 211c and an opposing lower side 211d that extend between the nasal end 211a and the temporal end 211b. When the underlid device 210 is deployed between the lower eyelid 12 and the eye surface 10c, the underlid device 210 is oriented as shown in FIG. 2A so that the upper side 211c is positioned closer to the cornea 10a and the lower side 211d is positioned farther from the cornea 10a. The upper side 211c is curved inwardly (toward the lower side 211d) to accommodate the shape of the lower eyelid 12. Correspondingly the lower side 211d is curved outwardly (away from the upper side 211c) to accommodate the shape of the lower region of the eye 10. The radius/radii of curvature for the lower side 211d may be similar to the radius/radii of curvature for the upper side 211c. In some embodiments, for instance, the upper side 211c and the lower side 211d are curved such that the distance from the uppermost point of the upper side 211c to the lowermost point of the lower side 211d is approximately 6 mm, and the distance from the lowermost point of the upper side 211c to the lowermost point of the lower side 211d is approximately 5.75 mm.

Figure 3B:
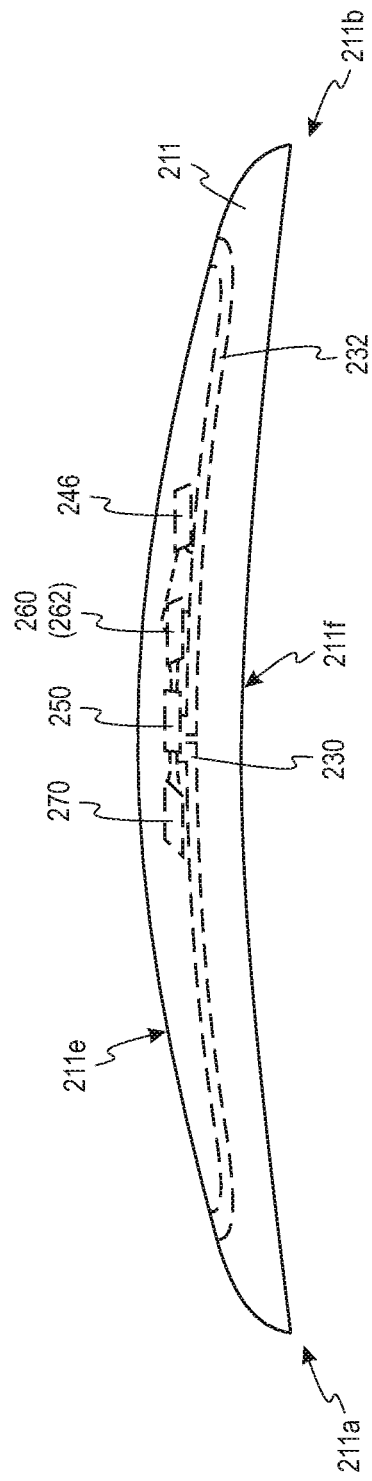
FIG. 3B illustrates a side view of the underlid device of FIG. 3A, according to aspects of the present disclosure.

FIG. 3B illustrates a side view of the underlid device 210. The body 211 includes an anterior surface 211e and an opposing posterior surface 211f that extend between the nasal end 211a and the temporal end 211b. When the underlid device 210 is deployed between the lower eyelid 12 and the eye surface 10c, the anterior surface 211e contacts the lower eyelid 12 and the posterior surface 211f contacts the eye surface 10c. To promote contact with the eye surface 10c, the posterior surface 211f has a generally concave shape that conforms to the contour of the sclera 10b at the lower region of the eye 10. The radius/radii of curvature for the concave shape of the posterior surface 211f defines the base curvature of the underlid device 210. The base curvature may include a single spherical radius or may include multiple curvatures or be described by an equation driven asphere.

As shown in FIG. 3B, an edge of the anterior surface 211e and an edge of the posterior surface 211f are joined at the perimeter of the underlid device 210. The junction between the anterior surface 211e and the posterior surface 211f can be characterized as the edge detail of the underlid device 210. The edge detail may be designed so that the perimeter of the underlid device 210 transitions more smoothly to the curvature of the eye surface 10c without an abrupt step. This enhances the comfort of wearing the underlid device 210, while also making the user aware that he/she is wearing the underlid device 210.

The body 211 has a thickness profile that is defined by the thicknesses, i.e., distances, between the anterior surface 211a and the posterior surface 211b. The thickness between the anterior surface 211a and the posterior surface 211b may vary across the body 211. The thickness profile may have a plurality of thickness regions with different respective thickness ranges. The thickness profile allows the underlid device 210 to fit stably and comfortably in the space between the lower eyelid 12 and the eye surface 10c. In general, the design and shape of the underlid device 210 may be characterized by the base curvature, the edge detail, and the thickness profile.

The underlid device 210 also includes a substrate 230, which includes aspects of the substrate 130 described above. The substrate 230 provides one or more surfaces for mounting a controller 250, bio-interactive electronics 260, an antenna 270, and a battery 246. The mounted elements 250, 260, 270, 246 include aspects of the respective elements 150, 160, 170, 146 described above. In particular, the bio-interactive electronics 260, i.e., the analyte sensor 262, is operable to measure analyte concentrations in the tear film in the biological environment to monitor health-related information. The antenna 270 may be employed to communicate the health-related information to the external processing device 180 via wireless signals 171 for further processing, presentation, and/or other task(s). The controller 250 controls the operation of the bio-interactive electronics 260 and the antenna 270. The battery 246 supplies operating voltages to the controller 250 and the bio-interactive electronics 260.

Figure 3C:
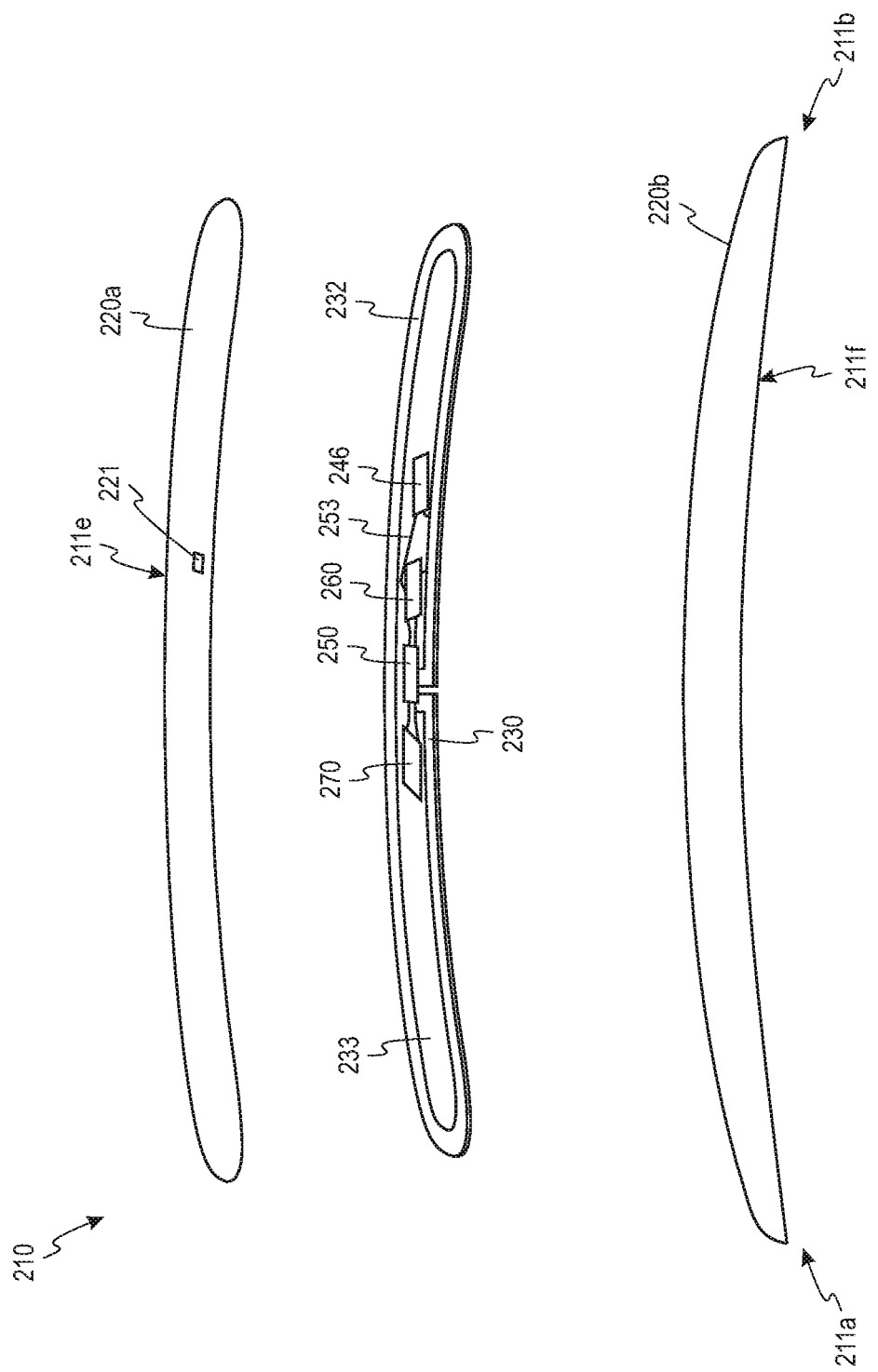
FIG. 3C illustrates an exploded view for an example assembly of the underlid device of FIG. 3A, according to aspects of the present disclosure.

According to some embodiments, the body 211 may be formed from more than one layer of the polymeric material 220. For instance, as shown in FIG. 3C, the substrate 230 may be disposed between a first polymer layer 220a and a second polymer layer 220b. In this way, the substrate 230 may be embedded in the body 211. With the substrate 230 embedded in the body 211, an opening 221 may be provided in the body 211, such as in the first polymer layer 220a, to expose aspects of the bio-interactive electronics 260, e.g., the analyte sensor 262, to the tear film.

The substrate 230 includes a supporting ring 232 that runs along the perimeter of the underlid device 210 to support the elements 250, 260, 270, 246. The width of the supporting ring 232 may be approximately 1 mm, for instance. The supporting ring 232 defines an inner opening 233.

Figure 3D:
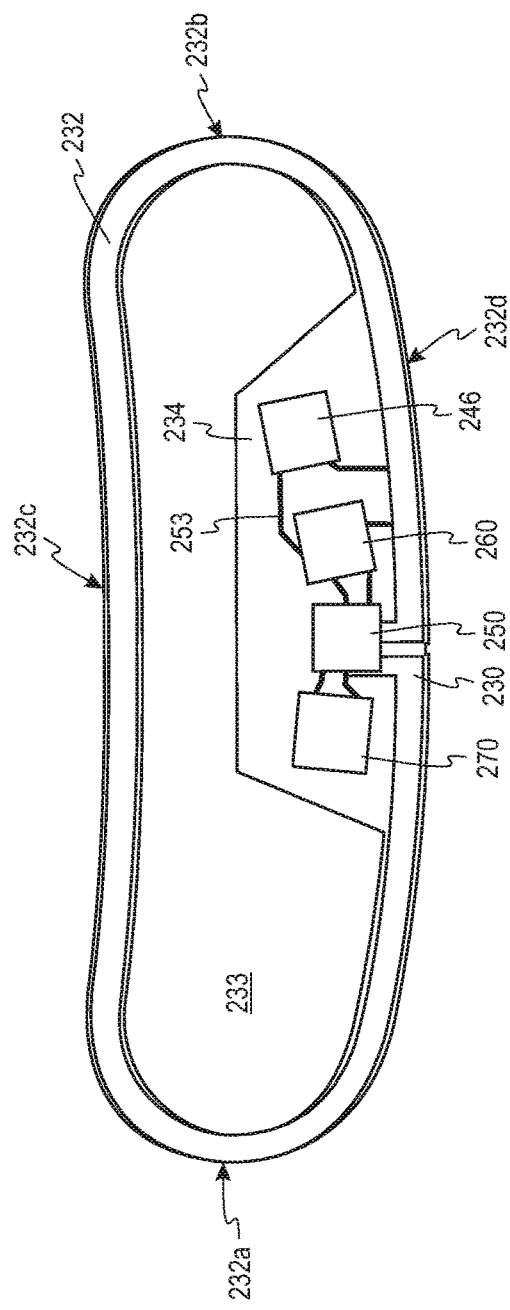
FIG. 3D illustrates an anterior view of an example substrate assembly for the underlid device of FIG. 3A, according to aspects of the present disclosure.

FIG. 3D illustrates an anterior view of the substrate 230. The shape of the supporting ring 232 may correspond to the shape of the body 211. In particular, the supporting ring 232 extends from a nasal end 232a to a temporal end 232b, which correspond to the nasal end 211a and the temporal end 211b, respectively. Similarly, when the underlid device 210 is deployed between the lower eyelid 12 and the eye surface 10c, the nasal end 232a is positioned closest to the nose of the user and the temporal end 232b is positioned closest to the temple of the user. At the nasal end 232a, the supporting ring 232 curves outwardly (away from the inner opening 233). Similarly, at the temporal end 232b, the supporting ring 232 curves outwardly (away from the inner opening 233).

The supporting ring 232 also includes an upper side 232c and a lower side 232d that extend between the nasal end 232a and the temporal end 232b. When the underlid device 210 is deployed between the lower eyelid 12 and the eye surface 10c, the upper side 232c is positioned closer to the cornea 10a and the lower side 232d is farther from the cornea 10a. The upper side 232c is curved inwardly (toward the inner opening 233) to accommodate the shape of the upper side 211c of the body 211, and the lower side 232d is curved outwardly (from the center of the inner opening 233) to accommodate the shape of the lower side 211d of the body 211.

The substrate 230 also includes a mounting platform 234 that extends from the supporting ring 232 into the inner opening 233. In particular, the mounting platform 234 may be positioned at the middle portion of the lower side 232d of the supporting ring 232, as shown in FIG. 3D. The controller 250, the bio-interactive electronics 260, the antenna 270, and the battery 246 are mounted on the mounting platform 234. The controller 250, the bio-interactive electronics 260, the antenna 270, and the battery 246 may be electrically connected via interconnects, which are shown collectively in FIG. 3D by reference numeral 253. In general, the substrate 230 may be employed for chip-based circuitry (e.g., by flip-chip mounting) and/or for patterning conductive materials (e.g., gold, platinum, palladium, titanium, copper, aluminum, silver, metals, other conductive materials, combinations of these, etc.) to create electrodes, interconnects, antennae, etc. The interconnects 253 which may formed by depositing suitable patterns of conductive materials on the substrate 230. A combination of resists, masks, and deposition techniques may be employed to pattern materials on the substrate 230.

Advantageously, the mounting platform 234 positions the bio-interactive electronics 260 where the analyte sensor 262 can maintain sufficient contact with the tear film and achieve consistent and accurate analyte concentration measurements. In particular, the bio-interactive electronics 260 are positioned at the middle portion of the lower side 232d of the supporting ring 232. As such, when the underlid device 210 is deployed between the lower eyelid 12 and the eye surface 10c, the bio-interactive electronics 260 are positioned closer to the bottom of the eye 10. In this position, a more predictable tear film layer is available to the analyte sensor 262, because the tear film layer experiences less exposure to air and other external conditions. In addition, pooling of tear solution may occur under the lower eyelid 12 and closer to the bottom of the eye 10, thereby providing a greater volume of tear solution for sampling. The tear film layer, for instance, may be at least approximately 10 µm.

As shown in FIG. 3D, the antenna 270 is positioned near the bio-interactive electronics 260 on the mounting platform 234. In general, the mounting platform 234 positions the antenna 270 where bone and tissue of the user's face does not interfere with the ability of the antenna 270 to receive a sufficiently strong signal.

To keep the bio-interactive electronics 260 and the antenna 270 on the same mounting platform 234, some of the signal strength received by the antenna 270 may be sacrificed in order to position the analyte sensor 262 at the desired tear film layer, e.g., closer to the bottom of the eye 10. In alternative embodiments, the mounting platform 234 may be positioned at another part of the supporting ring 232 to maintain greater signal strength while still exposing the analyte sensor 262 to a sufficient tear film layer. In other alternative embodiments, the bio-interactive electronics 260 and the antenna 270 may be positioned on separate mounting platforms at different parts of the supporting ring 232 to allow both signal strength and tear film sampling to be enhanced. For instance, the bio-interactive electronics 260 may be mounted on a first mounting platform closer to the lower side 232d of the supporting ring 232, while the antenna 270 may be mounted on a second mounting platform closer to the upper side 232c of the supporting ring 232.

As described above, the communication antenna 270 may be a dual-purpose antenna. In addition to communicating information between the underlid device 210 and the external processing device 180, the communication antenna 270 also functions as an energy-receiving antenna to capture energy the external processing device 180 via the wireless signals 171. Additionally, the battery 146 may be a rechargeable battery. As such, the antenna 270 may be employed to capture energy from the external processing device 180 to recharge the rechargeable battery.

In particular, after the antenna 270 receives radio frequency radiation from the external processing device 180, varying electrical signals on the leads of the antenna 270 are output to a rectifier/regulator. The rectifier/regulator conditions the captured energy to generate a stable recharging voltage for the battery 246. As long as the battery 246 retains some of the recharging voltage, the battery 246 can power the controller 250 and the bio-interactive electronics 260, even if the external processing device 180 is no longer in sufficient proximity to transmit radio frequency radiation to the antenna 270. The controller 250 and the bio-interactive electronics 260 can remain active as long as they receive the DC supply voltage from the battery 246. In other words, the battery 246 allows the underlid device 210 to be operated autonomously.

As described above, the controller 250 may include a sensor interface module to operate the analyte sensor 262 in order to monitor the analyte concentration in the tear film layer. Additionally, the controller 250 may continue to store sensor readings from the analyte sensor 262 until the external processing device 180 is in sufficient proximity and the sensor readings can be communicated to the external processing device 180 via the antenna 270.

Figure 3E:
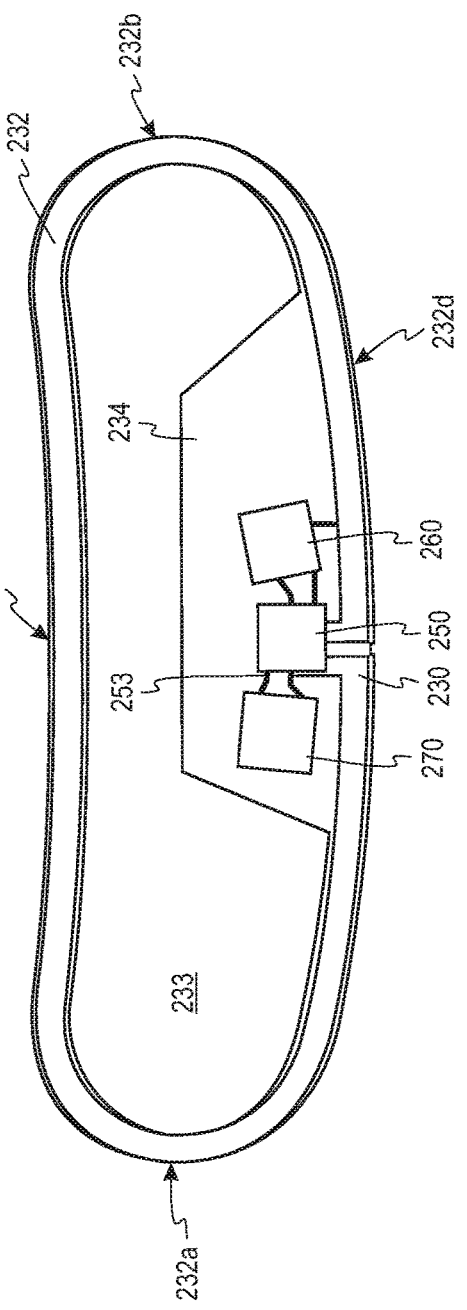
FIG. 3E illustrates an anterior view of an alternative substrate assembly for the underlid device of FIG. 3A, according to aspects of the present disclosure.

In alternative embodiments, the battery 246 is not employed to power the controller 250 and the bio-interactive electronics 260. Rather, the energy captured from the remote processing device 180 by the antenna 270 powers the controller 250 and the bio-interactive electronics 260 more directly. FIG. 3E illustrates the controller 250, the bio-interactive electronics 260, and the antenna 270 mounted on the mounting platform 234 of the substrate 230 without the battery 246. After the antenna 270 receives radio frequency radiation from the external processing device 180, varying electrical signals on the leads of the antenna 270 are output to a rectifier/regulator. The rectifier/regulator rectifies the varying electrical signals to a DC voltage and regulates the rectified DC voltage to a level suitable for operating the controller 250 and the bio-interactive electronics 260. Although these alternative embodiments may employ a simpler approach for powering the controller 250 and the bio-interactive electronics 260 without the battery 246, such an approach calls for the external processing device 180 to be in sufficient proximity to the underlid device 210 for the controller 250 and the bio-interactive electronics 260 to receive power for operation via the wireless signals. With this approach, the underlid device 210 is not operated autonomously. The external processing device 180 can control the operation of the underlid device 210 by actively controlling the transmission of the radio frequency radiation to the underled device 210. For instance, the radio frequency radiation can be considered an interrogation signal from the external processing device 180 to the eye-mountable device 110 to request measurement(s).

Figure 4A:
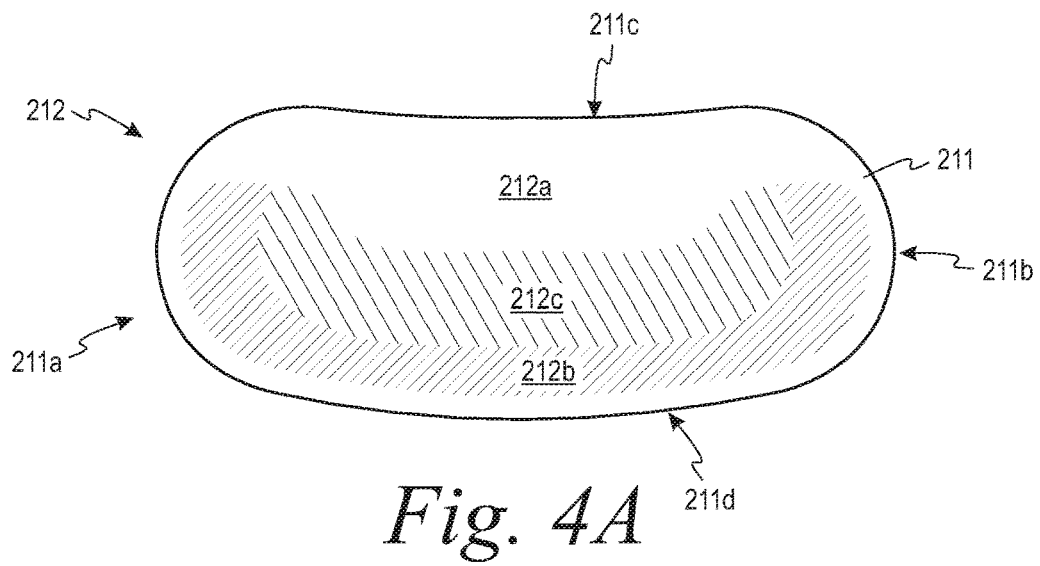
FIG. 4A illustrates an anterior view of an example thickness profile for the underlid device of FIG. 3A, according to aspects of the present disclosure.
Figure 4B:
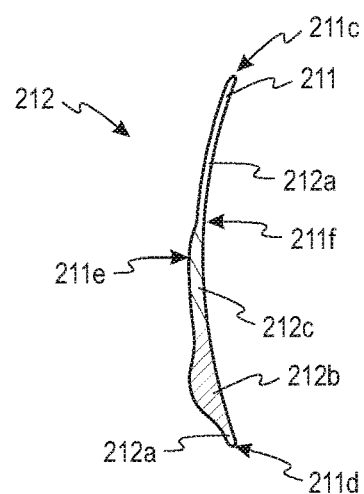
FIG. 4B illustrates a side view of the example thickness profile of FIG. 4A, according to aspects of the present disclosure.

As described above, the body 211 has a thickness profile that is defined by the thicknesses, i.e., distances, between the anterior surface 211a and the posterior surface 211b as shown in FIG. 3B. FIGS. 4A-B illustrate an example thickness profile 212 for the body 211.

FIG. 4A illustrates a top view of the underlid device 210 and FIG. 4B illustrates a side view of the underlid device 210. In particular, FIGS. 4A-B highlight three separate thickness regions 212a-c across the underlid device 210 for the thickness profile 212. The first thickness region 212a (no cross hatch) includes the perimeter of the underlid device 210 and extends inwardly from the upper side 211a to the middle of the underlid device 210 (between the upper side 211c and the lower side 211d). The second thickness region 212b (first cross hatch) extends just inside the perimeter of the underlid device 210 and proximally along the lower side 211d, the nasal end 211a, and the temporal end 211b. The third thickness region 212c (second cross hatch) includes the middle of the underlid device 210 and extends from the first thickness region 212a and to the second thickness region 212b.

The first thickness region 212a may have thickness(es) that fall in a range of approximately 100 µm to approximately 200 µm. As a part of the first thickness region 212a, the perimeter of the underlid device 210 transitions smoothly to the eye surface 10c, where the thickness may be approximately 100 µm. The second thickness region 212b may have thickness(es) that fall in a range of approximately 300 µm to approximately 1 mm. The third thickness region 212c may have thickness(es) that fall in a range of approximately 200 µm to approximately 300 µm. In general, the second thickness region 212b includes at least one thickness that is greater than the thicknesses of the first thickness region 212a and the third thickness region 212c, and the third thickness region 212c includes at least one thickness that is greater than the thickness(es) of the first thickness region 212a.

Advantageously, the thickness profile 212 allows the underlid device 210 to be positioned stably under the eyelid and minimizes upward or downward movement as well as movement in the direction of the user's nose or temple (nasal or temporal drift). In particular, the regions of greater thickness, e.g., the second thickness region 212b, enhance frictional contact with the lower eyelid 12 and the eye surface 10c, which resists the undesired movement or mechanical agitation. Additionally, the regions of greater thickness may provide greater weight near the middle of the lower side 211d to keep the underlid device centered and to prevent rotation of the underlid device 210.

As described above, mechanical agitation caused by blinking may generate noise in the sensor signals from the analyte sensor 262. Nasal or temporal drift may also cause the underlid device 210 to rotate and expose the analyte sensor 262 to air, which can result in cycles of dehydration/hydration that generate signal noise from the analyte sensor 262. Furthermore, the underlid device 210 may migrate deeper into the inferior fornix where the lower eyelid 14 and scleral conjuctiva meet. Movement into this region may interrupt or otherwise interfere with the wireless signal between the underlid device 210 and the external processing device 180.

Figure 4C:
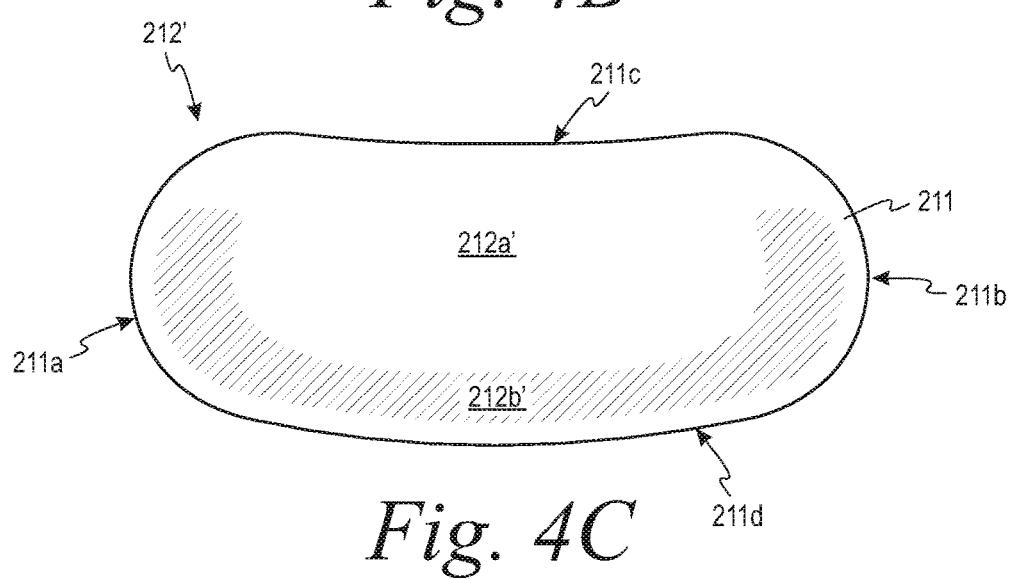
FIG. 4C illustrates an anterior view of another example thickness profile for the underlid device of FIG. 3A, according to aspects of the present disclosure.

Embodiments are not limited to the thickness profile 212 shown in FIGS. 4A-B. FIG. 4C, for instance, illustrates another thickness profile 212' for the underlid device 210. The thickness profile 212' includes two separate thickness regions 212a' and 212b' across the underlid device 210. The first thickness region 212a' (no cross hatch) includes the perimeter of the underlid device 210 and extends inwardly from the upper side 211a to the middle of the underlid device 210. The second thickness region 212b' (cross hatch) extends just inside the perimeter of the underlid device 210 and along the lower side 211d, the nasal end 211a, and the temporal end 211b. The underlid device 210 is thinnest at the first thickness region 212a', which may have thickness(es) in the range of approximately 100 µm to approximately 200 µm. As a part of the first thickness region 212a', the perimeter of the underlid device 210 transitions smoothly to the eye surface 10c, where the thickness may be approximately 100 µm. The thickness increases from the first thickness region 212a' to the second thickness region 212b', which may have thickness in the range of approximately 250 µm to approximately 1.0 mm. The second thickness region 212b' includes at least one thickness that is greater than the thickness(es) of the first thickness region 212a'.

In general, the thicker region(s) of the thickness profile enhance on-eye stability to keep the underlid device 210 central to the eye as much as possible and prevent the underlid device 210 from undesired movement to other parts of the eye. Additionally, the position of the thicker regions, e.g., along the lower side 211d, conveniently accommodates the mounting platform 234, where the controller 250, the bio-interactive electronics 260, the antenna 270, and optionally the battery 246 are mounted.

The substrate 230 is sufficiently thick to provide structural support for the mounted elements; at the same time, however, the substrate 230 can also be embedded in the polymeric material 220 without influencing the desired thickness profile of the underlid device 210. The substrate 230 may have a thickness of approximately 50 µm, for instance. Additionally, the antenna 270 may have a thickness of approximately 30 µm while the other elements 250, 260, 246 may have thicknesses of approximately 80 µm.

As shown in FIG. 3C, the substrate 230 may be disposed between a first polymer layer 220a and a second polymer layer 220b. At the thicker regions, e.g., second thickness region 212b', of at least 250 µm, the first polymer layer 220a may have a thickness of at least approximately 110 µm and the second polymer layer 220b may have a thickness of approximately 50 µm to approximately 60 µm to accommodate the substrate 230 and the elements mounted on the mounting platform 234. In addition, the first polymer layer 220a and/or the second polymer layer 220b may be thicker to make the thicker regions greater.

Aspects of the device 310 for the upper eyelid 14 shown in FIG. 2B can be understood from the description of the device 210 for the lower eyelid 12. In particular, it can be readily appreciated that the underlid device 310 may be similar to an upside-down implementation of the underlid device 210. However, it is understood that the specific design and shape, i.e., base curvature, edge detail, and thickness profile, of the underlid device 310 may differ to accommodate differences between the upper eyelid 14 and the lower eyelid 12.

IV. Conclusion

Underlid devices are configured to be positioned stably under the lower eyelid or upper eyelid. Advantageously, the underlid devices are deployed in positions that help minimize the effects of dehydration, mechanical agitation, light, and temperature. The underlid devices may have a thickness profile where the thicker region(s) of the thickness profile enhance on-eye stability and prevent the underlid devices from undesired movement to other parts of the eye.

It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

What is claimed is:

1. An eye-mountable device comprising:
    one or more layers of polymer material defining a body, the body including an upper edge and a lower edge, wherein the upper edge and lower edge both extend from a first end of the body to a second end of the body, the upper edge opposing the lower edge, the upper edge curving inwardly toward the lower edge, the lower edge curving outwardly away from the upper edge, the body including an anterior surface and a posterior surface that each extend from the first end to the second end and from the upper edge to the lower edge, the anterior surface opposing the posterior surface, the posterior surface having a concave shape, the body having a thickness profile defined by thicknesses from the anterior surface to the posterior surface, the thickness profile including a first thickness region having a first thickness range and a second thickness region having a second thickness range, a portion of the first thickness region extending along the upper edge, a first portion of the second thickness region extending along the lower edge between the lower edge and the portion of the first thickness region that extends along the upper edge, a second portion of the second thickness region extending from the first portion along the first end and a third portion of the second thickness region extending from the first portion along the second end such that the second thickness region has an arcuate shape, the second thickness range having at least one thickness that is greater than the first thickness range, and at least a portion of the first thickness region is located in an interior area of the arcuate shape;
    a substrate in the body including a mounting platform disposed proximally to a middle of the lower edge and closer to the lower edge than to the upper edge;
    bio-interactive electronics mounted on the mounting platform and disposed closer to the lower edge than to the upper edge, the bio-interactive electronics operable to interact with a biological environment external to the body and to monitor health-related information.

2. The eye-mountable device of claim 1, wherein the body includes a perimeter defined by the first end, the second end, the upper edge, and the lower edge, the perimeter at the first end curving outwardly away from the second end, and the perimeter at the second end curving outwardly away from the first end.

3. The eye-mountable device of claim 1, wherein the substrate includes a supporting ring extending along a perimeter of the body, the supporting ring defining an interior opening, the mounting platform extending from the supporting ring into the interior opening.

4. The eye-mountable device of claim 1, wherein the one or more polymer layers include a first polymer layer and a second polymer layer, the first polymer layer defines the anterior surface, and the second polymer layer defines the posterior surface, and the substrate is disposed between the first polymer layer and the second polymer layer.

5. The eye-mountable device of claim 1, further comprising an antenna operable to transmit the health-related information to an external processing device via wireless signals, the antenna mounted on the mounting platform and positioned to transmit the health-related information through an eyelid.

6. The eye-mountable device of claim 5, wherein the antenna is further operable and positioned to receive, through the eyelid, radio frequency radiation from the external processing device, the bio-interactive electronics receiving operating power based on the radio frequency radiation.

7. The eye-mountable device of claim 6, further comprising a rechargeable battery mounted on the mounting platform, the radio frequency radiation received by the antenna providing the operating power for the bio-interactive electronics via the rechargeable battery, wherein the radio frequency radiation provides recharging power to the rechargeable battery and the rechargeable battery provides the operating power to the bio-interactive electronics.

8. The eye-mountable device of claim 6, wherein the bio-interactive electronics receives the operating power only when the external processing device transmits the radio frequency radiation to the antenna.

9. An eye-mountable device comprising:
one or more layers of polymer material defining a body, the body including an upper edge and a lower edge that extend from a first end of the body to a second end of the body, the upper edge opposing the lower edge, the upper edge curving inwardly toward the lower edge, the lower edge curving outwardly away from the upper edge, the body including an anterior surface and a posterior surface that each extend from the upper edge to the lower edge and from the first end to the second end, the anterior surface opposing the posterior surface, the posterior surface having a concave shape, the body having a thickness profile defined by thicknesses from the anterior surface to the posterior surface, the thickness profile including a first thickness region having a first thickness range and a second thickness region having a second thickness range, a portion of the first thickness region extending along the upper edge, a first portion of the second thickness region extending proximately along the lower edge between the lower edge and the portion of the first thickness region that extends along the upper edge, a second portion of the second thickness region extending from the first portion along the first end and a third portion of the second thickness region extending from the first portion along the second end such that the second thickness region has an arcuate shape, the second thickness range having at least one thickness that is greater than the first thickness range, and at least a portion of the first thickness region is located in an interior area of the arcuate shape; and
bio-interactive electronics disposed in the body, wherein the bio-interactive electronics are operable to interact with a biological environment external to the body and to monitor health-related information, wherein the body includes a perimeter defined by the first end, the second end, the upper edge, and the lower edge, and wherein the second thickness region extends proximately along the perimeter on the outwardly curving lower edge, from the first end and the second end, and wherein the thickness profile includes a third thickness region having a third thickness range, the third thickness region being disposed between the first thickness region and the second thickness region, the third thickness range including at least one thickness that is greater than the first thickness range, the second thickness range including at least one thickness that is greater than the third thickness range, and at least a portion of the third thickness region being located within the interior area of the arcuate shape of the second thickness region.

10. The eye-mountable device of claim 9, wherein the bio-interactive electronics include an analyte sensor, wherein the analyte sensor is operable to determine a measurement of an analyte in the biological environment, the measurement being indicative of the health-related information.

11. The eye-mountable device of claim 9, wherein the perimeter at the first end curves outwardly away from the second end, and the perimeter at the second end curves outwardly away from the first end.

12. The eye-mountable device of claim 9, wherein the first thickness range includes one or more thicknesses in a range of 100 μm to 250 μm, and the second thickness range includes one or more thicknesses in a range of 250 μm to 1.0 mm.

13. The eye-mountable device of claim 9, wherein the first thickness region extends along the perimeter.

14. The eye-mountable device of claim 13, wherein the first thickness region has a thickness of 100 μm at the perimeter.

15. The eye-mountable device of claim 13, wherein an edge of the anterior surface and an edge of the posterior surface are joined at the perimeter of the body.

16. The eye-mountable device of claim 9, wherein the first thickness range has one or more thicknesses in a range of 100 μm to 200 μm, the second thickness range has one or more thicknesses in a range of 300 μm to 1.0 mm, and the third thickness range has one or more thicknesses in a range of 200 μm to 300 μm.

17. The eye-mountable device of claim 9, wherein the bio-interactive electronics are disposed within the second thickness region.

* * * * *